(12) United States Patent
Beoni

(10) Patent No.: US 8,764,826 B2
(45) Date of Patent: Jul. 1, 2014

(54) MIDDLE EAR PROSTHETIC DEVICE

(76) Inventor: Franco Beoni, Piacenza (IT)

( * ) Notice: Subject to any disclaimer, the term of this patent is extended or adjusted under 35 U.S.C. 154(b) by 1131 days.

(21) Appl. No.: 12/362,348

(22) Filed: Jan. 29, 2009

(65) Prior Publication Data

US 2010/0100180 A1    Apr. 22, 2010

(30) Foreign Application Priority Data

Oct. 21, 2008 (EP) .................................... 08167187

(51) Int. Cl.
*A61F 2/18* (2006.01)

(52) U.S. Cl.
USPC .............................................. 623/10; 600/25

(58) Field of Classification Search
USPC .................. 623/10; 606/57; 600/25
See application file for complete search history.

(56) References Cited

U.S. PATENT DOCUMENTS

| | | | | |
|---|---|---|---|---|
| 3,196,462 | A * | 7/1965 | Mendell | 623/10 |
| 3,473,170 | A * | 10/1969 | Haase et al. | 623/10 |
| 3,909,852 | A * | 10/1975 | Homsy | 623/10 |
| 4,130,905 | A * | 12/1978 | Mercandino | 623/10 |
| 4,601,723 | A * | 7/1986 | McGrew | 623/10 |
| 4,921,498 | A * | 5/1990 | Bays et al. | 623/10 |
| 5,180,391 | A | 1/1993 | Beoni | |
| 5,514,177 | A * | 5/1996 | Kurz et al. | 623/10 |
| 5,941,814 | A * | 8/1999 | Lehner et al. | 600/25 |
| 6,387,128 | B1 * | 5/2002 | Kurz et al. | 623/10 |
| 6,432,139 | B1 * | 8/2002 | Elies et al. | 623/10 |
| 7,806,931 | B2 * | 10/2010 | Huettenbrink et al. | 623/10 |
| 8,221,497 | B2 * | 7/2012 | Beoni | 623/10 |
| 2002/0045939 | A1 * | 4/2002 | Kurz | 623/10 |
| 2004/0162614 | A1 * | 8/2004 | Steinhardt et al. | 623/10 |
| 2006/0161255 | A1 * | 7/2006 | Zarowski et al. | 623/10 |
| 2007/0255405 | A1 | 11/2007 | Reitan et al. | |
| 2008/0195201 | A1 | 8/2008 | Steinhardt et al. | |
| 2008/0234817 | A1 * | 9/2008 | Huettenbrink et al. | 623/10 |
| 2009/0164010 | A1 * | 6/2009 | Steinhardt et al. | 623/10 |
| 2010/0010629 | A1 * | 1/2010 | Bhansali | 623/10 |
| 2011/0066240 | A1 * | 3/2011 | Beoni | 623/10 |

FOREIGN PATENT DOCUMENTS

EP        0 460 354 A2    12/1991

* cited by examiner

*Primary Examiner* — Paul Prebilic
(74) *Attorney, Agent, or Firm* — Novak Druce Connolly Bove + Quigg LLP

(57) ABSTRACT

A middle ear prosthetic device including: a columellate prosthesis, one end of which is connectable to the stapes or to its remaining footplate; an annular element of bioinert metal insertable into the auditory tube after suitable milling; an elastic elongated element of bioinert material, disposed transversely to the annular element, a first end of the elongated element being rigid with the annular element while its second end is free and to it there being connected the other end of the columellate prosthesis; for supporting the neotympanum, a tensostructure of wires of non-reabsorbable bioinert material fixed taut to the interior of the annular element to support the neotympanum, the distance between the wires being such as to provide the surgeon with a sufficient view of the surgical field, the elongated elastic element interfering with the tensostructure.

15 Claims, 3 Drawing Sheets

MIDDLE EAR PROSTHETIC DEVICE

This application claims the priority of European Patent Application No. 08167187.7 filed on 21 Oct. 2008.

The present invention relates to a middle ear prosthetic device.

As known to the expert of the art, reconstructive interventions on the middle ear are principally of two types, specifically:
1. stapedotomy for otosclerosis; and
2. tympano-ossiculoplasty for chronic otitis.

Stapedotomy intervention consists of replacing the stapes ossicle, blocked by the effect of otosclerosis, and enables only the footplate to be preserved, which however is bored. The function of transmitting the sound wave from the incus to the inner ear is performed by using a columellate prosthesis, having its outermost end coupled to the incus and an innermost end inserted into the hole formed in the footplate, to hence transmit the sound wave directly to the inner ear.

This intervention enables hearing recovery to be achieved in about 95% of cases, this recovery remaining constant with time as the prosthesis is coupled to the incus and cannot move.

Tympano-ossiculoplasty intervention consists of replacing the tympanum with tissue taken from the patient, and replacing the ossicular chain with a columellate prosthesis (ossiculoplasty), possibly using the stapes, if still totally present, or its footplate.

In ossiculoplasty the prosthesis is inserted between the neotympanum and, respectively, the capitellum of the stapes or its footplate. However, the prosthesis rests with slight pressure (evidently not being able to be suspended from the neotympanum) on the stapes or on the footplate, respectively. Precisely for this reason, in tympano-ossiculoplasty the footplate of the stapes is not bored (as is done in stapedectomy), to prevent the prosthesis descending by gravity into the inner ear, with the risk of serious complications such as vertigo and deafness. Consequently during tympano-ossiculoplasty the columellate prosthesis can only be rested on the stapes capitellum or alternatively on its footplate, which however results in poor sound transmission to the inner ear and hence poor hearing recovery.

It should also be noted that because of the presence of the neotympanum, the surgeon does not have a good view of the operative field, hence errors can arise in positioning the columellate prosthesis on the capitellum or on the stapes footplate respectively, resulting in an unsuccessful intervention.

Moreover, even if the positioning of the columellate prosthesis is correct, in a large number of cases this prosthesis can become displaced with time, with consequent worsening of the hearing.

A first attempt to form a middle ear prosthesis able to give functional results comparable to those obtained by stapedectomy was made with the prosthetic device described in EP-B-0460354.

This device essentially comprises a tympanic prosthesis composed of an annular element, an elastic membrane fixed to the annular element, and a columellate prosthesis fitted to the tympanic prosthesis. The annular element is of a material able to be fixed to the bone tissue of the auditory tube when positioned in contact therewith following milling. Connection means enable the distal end of the columellate prosthesis to be connected to the central region of the membrane.

The other end of the columelate prosthesis is connected to the stapes or to its footplate.

This middle ear prosthetic device has been used in many patients for some ten years, but has not produced the hoped-for results because of implant difficulties and in particular the impossibility of positioning the columellate prosthesis in the hole made in the footplate (it would sink into the inner ear with the already stated negative consequences) and the consequent difficulty of maintaining it in the required position until fitted to the tympanic prosthesis. In this respect, it was found necessary to initially position the columellate prosthesis and only later to position the tympanic prosthesis and finally fit the two prostheses together. Fitting the columellate prosthesis and tympanic prosthesis was achieved by pressing on the columellate prosthesis, this pressing which besides being traumatic had to be done without the aid of visual checking, as the tympanic prosthesis covered the underlying surgical field, making it difficult to control the columellate prosthesis.

An object of the present invention is to provide a middle ear prosthetic device which enables the surgeon, during the tympanoplastic intervention, to have a view of the operational field such as to enable the footplate hole to be made and the columellate prosthesis to be correctly positioned in said hole. In other words, the prosthetic device must enable the surgeon to achieve—even for middle ear interventions aimed at remedying the consequences of destruction of the ossicular chain caused by chronic otitis—an operational field similar to that which the surgeon has during a stapedotomy intervention for otosclerosis. If such a prosthetic device were achieved, it would become possible to obtain a hearing recovery in around 95% of cases even in tympano-ossiculoplasty interventions. Another object of the invention is to provide a middle ear prosthetic device which enables the hearing recovery obtained following the tympano-ossiculoplasty intervention to remain constant with time.

These objects are attained by the middle ear prosthetic device of the present invention, comprising:
- a columellate prosthesis arranged to replace, in sound wave transmission, the ossicular chain of the middle ear with the exception of the stapes or at least its footplate, one end of this prosthesis being connectable to the stapes or its footplate;
- an annular element of bioinert metal insertable, by previous milling, into the auditory tube at the position in which the neotympanum is to be formed; characterised by further comprising:
- an elastic elongated element of bioinert material, disposed transversely to the annular element, a first end of the elongated element being rigid with the annular element while its second end is free, at or in the vicinity of this second end there being connected the other end of said columellate prosthesis;
- for supporting the neotympanum, a tensostructure of wires of non-reabsorbable bioinert material, which extends to the interior of the annular element and is fixed to this latter, the distance between the wires being such as to provide the surgeon with a sufficient view of the surgical field and allow the required surgical manoeuvres, the elongated elastic element interfering with the tensostructure.

From the aforegoing an expert of the art will understand that the annular element together with the elongated elastic element and the tensostructure essentially form a tympanum and incus prosthesis (the neotympanum, of the patient's tissue, resting on the tensostructure only at the end), which supports the columellate prosthesis.

The wires used for forming said tensostructure are conveniently surgical wires of a non-reabsorbable bioinert polymer.

Said elongated elastic element is preferably a piece of nitinol wire (titanium/nickel alloy) of the so-called superelastic type, but could for example also be of stainless steel.

A means is conveniently provided for retaining the elongated elastic element in a non-deformed position during application of said columellate prosthesis. If only the stapes footplate is present, the columellate prosthesis can be of conventional type, i.e. having a hook-shaped distal end (for connection to said elongated elastic element), while the vicinal end is shaped for insertion into a hole previously provided in the footplate.

If instead the entire stapes is still present, a columellate prosthesis is used in which the distal end is again of hook shape while the vicinal end is shaped (for example cup-shaped) to be able to be mounted over the stapes capitellum.

By virtue of the prosthetic device of the present invention, correct positioning of one or other type of said columellate prosthesis can be achieved by the surgeon without particular difficulty and be visually checked thereby as the distance between the wires of said tensostructure is such as to enable operation through the free spaces between the wires.

Said tensostructure is conveniently a weave of wires, i.e. formed from two crossing sets of wires suitably spaced apart. However the tensostructure can also be formed from only a single set of parallel wires.

The invention will be more apparent from the ensuing description of one embodiment thereof. In this description reference is made to the accompanying drawings, in which.

Figure 1:
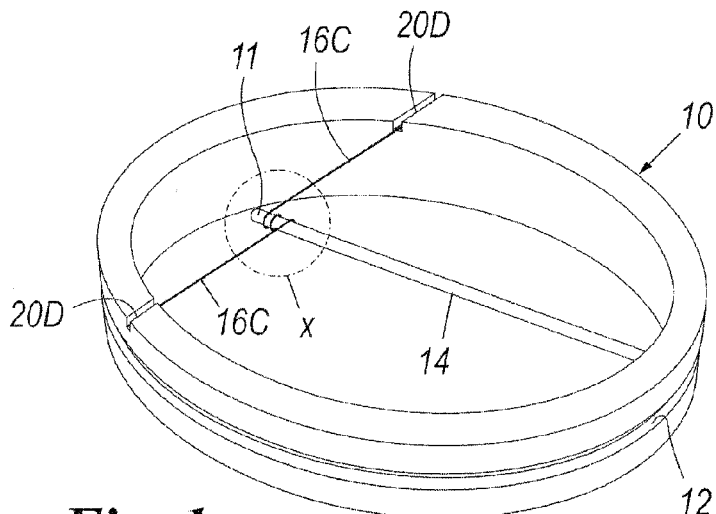
FIG. 1 is a perspective view, enlarged compared with reality, of a part of the middle ear prosthetic device of the invention, the figure showing the annular element and the elastic elongate element with said relative retention means, whereas said tensostructure is not shown for simplicity and to maintain clarity.
Figure 1A:
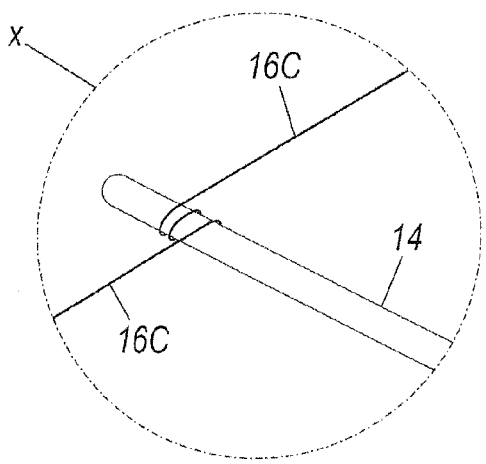
FIG. 1A is an enlarged view showing the detail X of FIG. 1.

As already stated, the prosthetic device of the invention comprises an annular element, indicated by 10 in FIG. 1, intended to be located by the surgeon in the patient's auditory tube after reaming by conventional millers to enable it to be inserted in position. The annular element 10 is of a bioinert metal (for example titanium ASTM F67, group 2) and presents in its outer edge an annular groove 12 such that with the passage of time bone tissue re-grows within it to hence prevent movement of the annular element 10.

Figure 2:
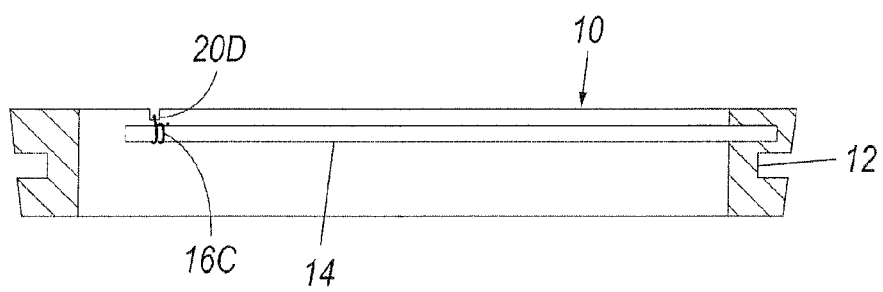
FIG. 2 is a coaxial cross-section through the annular element of FIG. 1.

FIGS. 1 and 2 show that an elongated elastic element 14 extends diametrically from the inner side of the annular element 10 and has one end rigid with the annular element 10 while its other end is free.

The elongated element 14 is of an elastic bioinert metal, in particular a piece of nitinol wire of the so-called super-elastic type (produced for example by Nitinol Devices & Components, California, USA).

Figure 3:
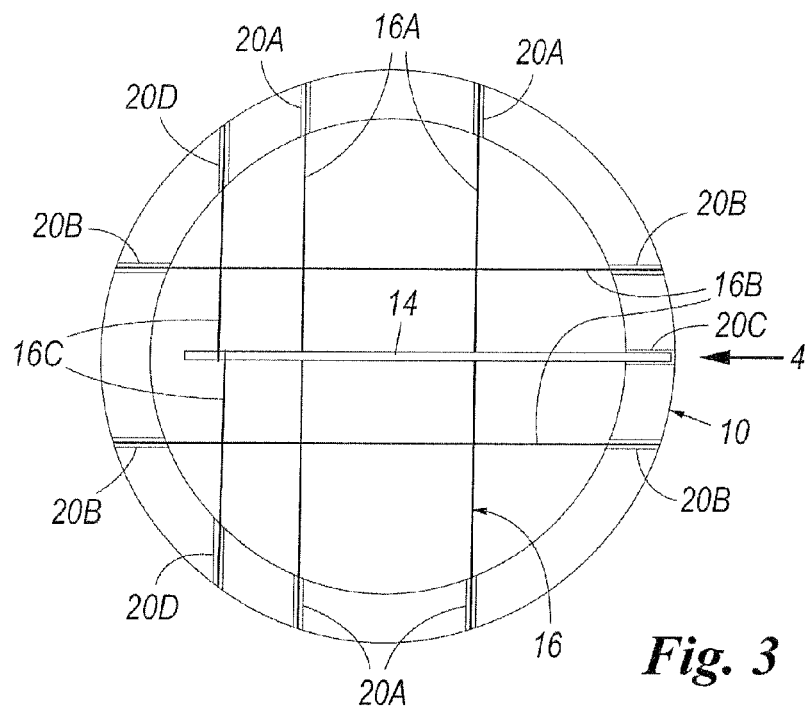
FIG. 3 is a view of the annular element and relative elongated elastic element from above, including said wire tensostructure and said elastic element retention means.
Figure 4:
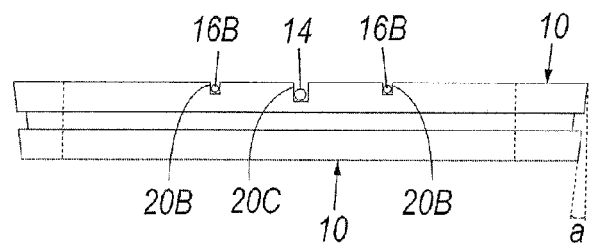
FIG. 4 is a view thereof in the direction of the arrow 4 of FIG. 3.
Figure 5:
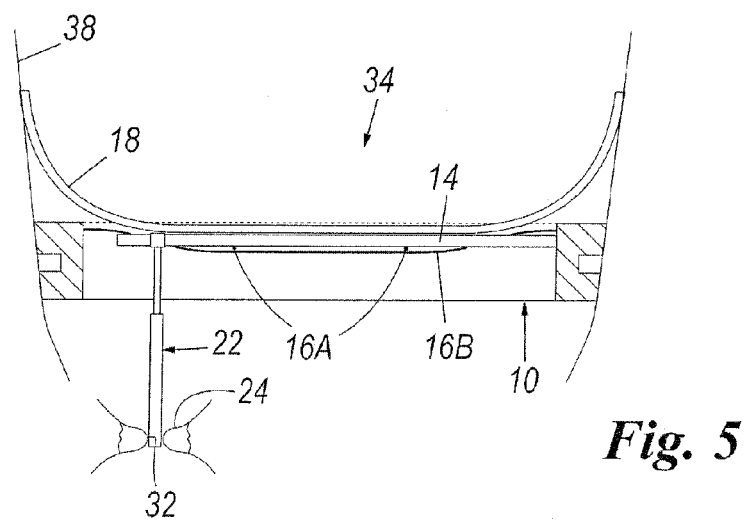
FIG. 5 is a section through part of the auditory tube and of the relative tympanum case on termination of the intervention, certain dimensions having been altered in the figure for clarity.

As shown in FIGS. 3 and 4, a tensostructure 16, formed from a weave of wires 16A and 16B is fixed taut to the annular element 10 for the purpose of supporting the neotympanum (indicated in FIG. 5 by 18). This latter is reconstructed from tissue of the actual patient by a classical surgical technique. The wires 16A and 16B are in this specific case of the non-reabsorbable type used for surgical sutures. It should be noted that although the wires 16A and 16B are shown mutually perpendicular in FIG. 3, they could also form angles other than a right angle, and that the elongated elastic element 14 need not be parallel to the wires 16B.

As also shown in FIGS. 3 and 4, the ends of the wires 16A and 16B are inserted into relative cavities, 20A and 20B respectively, provided in the annular element 10, in which cavities these ends are locked by deformation (not shown for simplicity) of the metal surrounding the cavity. The same figures also show that a cavity 20C is also provided for receiving that end of the elongated element 14 intended to be fixed into the annular element 10, this fixing again being conveniently achieved by deformation (again not shown) of the metal surrounding the cavity 20C. Consequently the elongated elastic element 14 behaves from the static viewpoint as a bracket projecting diametrically from the inner face of the annular element (FIG. 3). As can be seen from FIGS. 3 and 5, the elongated elastic element 14 interferes with the weave 16 by resting on the wires 16A. This weave also prevents excessive flexure of the elongated elastic element 14 towards the inner ear, so preventing the vicinal end 30 of the columellate prosthesis 22 (shown very schematically in FIG. 3) from penetrating into the inner ear through the hole 32 formed in the stapes footplate 24.

FIG. 3 also shows that about the free end of the elongated elastic element 14 there is wound a wire 16C the two ends of which are inserted into respective cavities 20D in which these ends are locked, again by deformation of the adjacent metal of the annular element 10, taking care that the wire 16C is under tension. The wire 16C (also conveniently of the type used for surgical sutures) forms said means for retaining the elongated elastic element 14 in its non-deformed position, for the purpose of preventing its deformation until a conventional columellate prosthesis 22 has been mounted on its free end to replace the ossicular chain and suitable for the situation in which only the stapes footplate 24 has remained.

Figure 7:
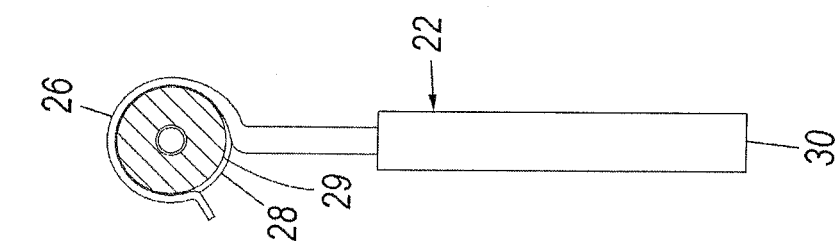
FIG. 7 shows the same prosthesis rotated through 90°.
Figure 6:
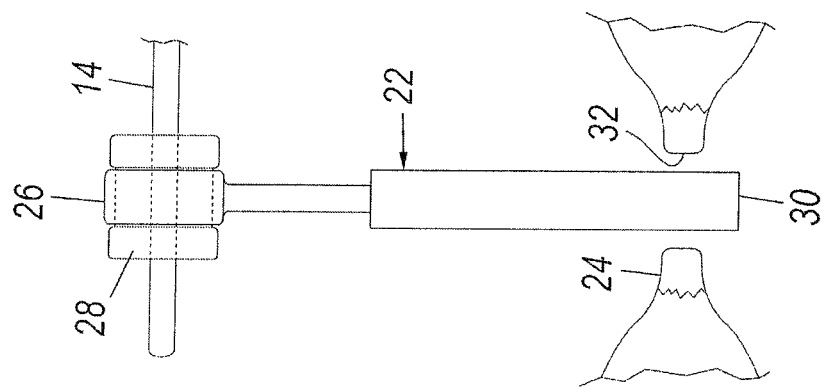
FIG. 6 is an even more enlarged view of a conventional columellate prosthesis forming part of a prosthetic device of the present invention, this prosthesis being of the type suitable for the situation in which only the stapes footplate remains.

The columellate prosthesis 22 is shown in greater detail in FIGS. 6 and 7, from which it can be seen that it is provided with a hook 26 enabling it to be hung from the elongated elastic element 14 on which a sleeve 28 of biocompatible material (for example a conventional biocompatible polymer) has been previously mounted. The sleeve 28 presents an intermediate part 29 of lesser diameter, on which intermediate part the hook 26 is coupled and tightened. As already stated, the lower end 30 of the columellate prosthesis 22 is intended to be inserted into a hole 32 previously made in the stapes footplate 24. As the prosthesis 22 is hung from the elongated elastic element 14, the free end of which is retained by the wire 16C, it is not possible, during application of the columellate prosthesis 22, for its vicinal end 30 to sink into the inner ear. When the prosthesis 22 has been positioned as shown in FIG. 5, the two arms of the wire 16C have merely to be cut to release the elongated elastic element 14 and enable the prosthetic device of the invention (indicated overall by 34 in FIG. 5) to operate.

Figure 8:
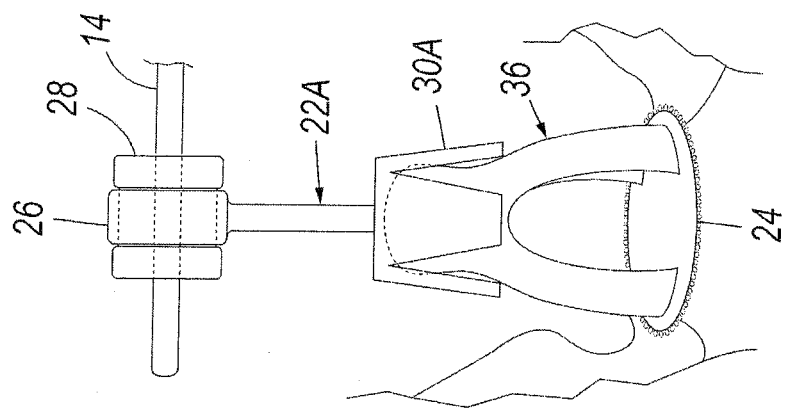
FIG. 8 shows a columellate prosthesis of the type suitable for the situation in which the entire stapes is still present.

If the entire stapes is still present, a columellate prosthesis 22A (FIG. 8) is used which differs from the prosthesis 22 by having its vicinal end shaped so that it can be mounted on the capitellum of the stapes 36, as shown in FIG. 8.

By way of example and with reference to FIGS. 3-5, the annular element 10 can be formed with an outer conicity (a) of 2° and have an outer diameter from 8.0 to 13.0 mm, depending on the patient. Preferably an entire series of annular elements will be made available with their outer diameter differing by 0.5 mm. The cross-section of the annular element 10 can for example have a height of 1.0 mm and a width at its top of 0.6 mm. The outer annular groove 12 can have a height of 0.3 mm and a depth of 0.2 mm. The thickness of the superelastic nitinol wire can for example be of 0.2 mm. In any event it must have a flexibility such as to enable the elongated elastic element 14 to follow the vibrations of the neotympanum 18.

A brief description will now be given of how the middle ear prosthetic device 34 is applied to the patient.

The surgeon firstly executes the classical steps of tympanoplasty, to amply expose the outer auditory tube, which is reamed with conventional millers, then completing reaming with suitable diamond-clad millers (see EP-B-0460354). At this point the annular element 10 already provided with the tensostructure 16 and the elongated elastic element 14 with the relative retention wire 16C is inserted. Using a microgripper, the surgeon rotates the annular element 10 to orientate it such that the elongated elastic element 14, which extends diametrically, traverses the stapes area.

The columellate prosthesis 22 can now be located in position (FIGS. 6 and 7) by coupling it initially to the elongated elastic element 14 using the relative hook 26 (possibly providing said coupling sleeve 28), to then insert the vicinal end 30 of the prosthesis 22 into the through hole 32 previously provided in the stapes footplate 24. The hole is made using a suitable conventional laser. Finally, the hook 26 is tightened to prevent movement of the prosthesis along the elongated elastic element 14. It should be noted that in some cases it could be necessary or convenient to replace the stapes footplate 24 by a strip of the patient's tissue (for example a strip of vein), the prosthesis 34 remaining however unaltered.

It should be noted that the purpose of the retention wire 16C is both to maintain the elongated elastic element 14 at rest while the columellate prosthesis 22 is being located in position, and to prevent the vicinal end 30 of the prosthesis from dipping into the inner ear through the hole 32 during said operation (to prevent those serious problems well known to the expert of the art).

It should also be noted that the purpose of the weave 16 is both to support the neotympanum 18 which is subsequently rested on it, and to prevent the neotympanum 18, spontaneously or by possible traumas, from approaching the base of the tympanic case and cause downward deformation of the elongated elastic element 14 and consequently of the prosthesis 22, this causing the undesirable dipping of its end 30 into the inner ear.

Figure 9:
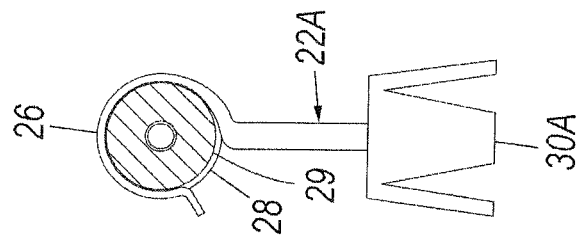
FIG. 9 shows only this latter prosthesis rotated through 90°.

It is important to note that because of the large distance between the wires 16A and 16B and the relative thinness of the elongated elastic element 14 the surgeon has a good view of the underlying surgical field, so that there is no difficulty in making the through hole 32 in the footplate 24 with the laser, or in locating the prosthesis 22 in the correct position, or in tightening its hook 26. As already stated, if the entire stapes 36 is still present (FIG. 8), the prosthesis will be of the type 22A shown in FIGS. 8 and 9, provided with a vicinal end shaped roughly as a cup, to be able to be drawn over the capitellum of the stapes 36.

In both cases, once the two branches of the retention wire 16C have been cut, and after the tympanic neomembrane 18 has been applied by known methods to rest on the weave 16, the intervention can be considered concluded.

The invention claimed is:

1. A middle ear prosthetic device, comprising:
 a columellate prosthesis arranged to replace, in sound wave transmission, an ossicular chain of a middle ear with the exception of a stapes or at least a footplate of the stapes, a first end of the columellate prosthesis being connectable to the stapes or to the footplate;
 an annular element of bioinert metal insertable, by previous milling, into the an auditory tube at a position in which a neotympanum is to be formed, the neotympanum for functionally replacing a tympanum of the middle ear;
 an elastic elongated element of bioinert material, disposed transversely to the annular element, a first end of the elongated element being coupled to the annular element while a second end of the elongated element is spaced from the annular element to be free relative to the annular element, the elastic elongated element being connectable to a second end of said columellate prosthesis at or in a vicinity of the second end of the elastic elongated element;
 a tensostructure of wires of non-reabsorbable bioinert material, which extends through an interior of the annular element and is fixed to the annular element, the tensostructure of wires for supporting the neotympanum on a side of the tensostructure distal to the inner ear when the neotympanum is formed, wherein a distance between the wires being for providing a surgeon with a sufficient view of a surgical field and allowing required surgical maneuvers, the elongated elastic element interfering with the tensostructure;
 wherein the columellate prosthesis being configured to hang from the elastic elongated element;
 wherein each said wire of said tensostructure has a first end and a second end, wherein each said wire first end and each said wire second end is directly attached to said annular element to be under tension.

2. The middle ear prosthetic device as claimed in claim 1, wherein the wires of the tensostructure are surgical wires of a bioinert polymer.

3. The middle ear prosthetic device as claimed in claim 1, wherein the elongated elastic element is a piece of nitinol wire.

4. The middle ear prosthetic device as claimed in claim 1, wherein a means is provided for retaining the elongated elastic element in position during application of the columellate prosthesis.

5. The middle ear prosthetic device as claimed in claim 1, wherein the second end of the columellate prosthesis to be connected to the second end of the elongated elastic element is shaped as a hook.

6. The middle ear prosthetic device as claimed in claim 3, wherein the second end of the columellate prosthesis to be connected to the elongated elastic element is shaped as a hook, and wherein the middle ear prosthetic device further comprises a sleeve of bioinert material interposed between the hook of the columellate prosthesis and the piece of nitinol wire of the elongated elastic element, wherein an intermediate part of the sleeve to which the hook is coupled is of reduced diameter.

7. The middle ear prosthetic device as claimed in claim 1, wherein the first end of the columellate prosthesis is shaped for insertion into a hole provided in the footplate of the stapes.

8. The middle ear prosthetic device as claimed in claim 1, wherein the end of the columellate prosthesis is shaped as a cup, to be drawn over the capitellum of the stapes.

9. The middle ear prosthetic device as claimed in claim 1, wherein the annular element comprises an annular groove defined along an outer lateral surface of the annular element.

10. The middle ear prosthetic device as claimed in claim 9, wherein the outer lateral surface of the annular element is provided with a conicity of 2°.

11. A middle ear prosthetic device, comprising:
a columellate prosthesis arranged to replace, in sound wave transmission, an ossicular chain of a middle ear with the exception of a stapes or at least a footplate of the stapes, a first end of the columeliate prosthesis being connectable to the stapes or to the footplate;
an annular element of bioinert metal insertable, by previous milling, into an auditory tube at a position in which a neotympanum is to be formed, the neotympanum for functionally replacing a tympanum of the middle ear;
an elastic elongated element of bioinert material, disposed transversely to the annular element, a first end of the elongated element being coupled to the annular element white a second end of the elongated element is spaced from the annular element to be free relative to the annular element, the elastic elongated element being connected to a second end of said columellate prosthesis at or in a vicinity of the second end of the elastic elongated element;
a tensostructure of wires of non-reabsorbable bioinert material, which extends to an interior of the annular element and is fixed to the annular element, the tensostructure of wires for supporting the neotympanum on a side of the tensostructure distal to the inner ear when the neotympanum is formed, wherein a distance between the wires being for providing a surgeon with a sufficient view of a surgical field and allowing required surgical maneuvers, the elongated elastic element interfering with the tensostructure;
wherein the columellate prosthesis hangs from the elastic elongated element;
wherein about the second end of the elongated elastic element there is wound a wire of the tensostructure of wires wherein opposed ends of the wound wire are directly attached to the annular element.

12. A middle ear prosthetic device, comprising:
a columellate prosthesis arranged to replace, in sound wave transmission, an ossicular chain of a middle ear with the exception of a stapes or at least a footplate of the stapes, a first end of the columeliate prosthesis being connectable to the stapes or to the footplate;
an annular element of bioinert metal insertable, by previous milling, into an auditory tube at a position in which a neotympanum is to be formed, the neotympanum for functionally replacing a tympanum of the middle ear;
an elastic elongated element of bioinert material disposed transversely to the annular element, a first end of the elongated element being coupled to the annular element while a second end of the elongated element is spaced from the annular element to be free relative to the annular element, the elastic elongated element being connected to a second end of said columellate prosthesis at or in a vicinity of the second end of the elastic elongated element;
a tensostructure of wires of non-reabsorbable bioinert material, which extends to an interior of the annular element and is fixed to the annular element, the tensostructure of wires for supporting the neotympanum on a side of the tensostructure distal to the inner ear when the neotyrnpanum is formed, wherein a distance between the wires being for providing a surgeon with a sufficient view of a surgical field and allowing required surgical maneuvers, the elongated elastic element interfering with the tensostructure;
wherein the columellate prosthesis hangs from the elastic elongated element;
wherein about the second end of the elongated elastic element there is wound a wire of the tensostructure of wires wherein opposed ends of the wound wire are inserted into cavities of the annular element into which the ends of the wound wires are locked.

13. A middle ear prosthetic device as claimed in claim 1, wherein the annular element is sized for extending transversely across the auditory tube at the position in which the neotympanum is to be formed.

14. A middle ear prosthetic device as claimed in claim 1, wherein the annular element has an outer diameter of 8.0 to 13.0 mm.

15. A middle ear prosthetic device as claimed in claim 1,
wherein the tensostructure of wires has opposed first and second sides, the first side of the tensostructure of wires for supporting the neotympanum to be formed over the tensostructure of wires, and
the columellate prosthesis second end is connectable to the second end of the elastic elongated element at or in the vicinity of the second end of the elastic elongated element and the columellate prosthesis is for extending away from the elongated element in a direction away from the tensostructure of wires with the first end of the columeilate prosthesis below the tensostructure of wires, the elongated element contacts the first side of the tensostructure of wires.

* * * * *